United States Patent [19]

Everly

[11] Patent Number: 4,611,075

[45] Date of Patent: Sep. 9, 1986

[54] PREPARATION OF 4-(α,α-DIHYDROCARBYL-α-CYANO-METHYL)PHENOLS

[75] Inventor: Charles R. Everly, Baton Rouge, La.

[73] Assignee: Ethyl Corporation, Richmond, Va.

[21] Appl. No.: 722,284

[22] Filed: Apr. 11, 1985

Related U.S. Application Data

[62] Division of Ser. No. 552,283, Nov. 16, 1983, abandoned.

[51] Int. Cl.$^4$ ............................................. C07C 120/00
[52] U.S. Cl. ..................................... 558/351; 558/410
[58] Field of Search ........... 260/465 F, 465 D, 465 E; 558/351

[56] References Cited

U.S. PATENT DOCUMENTS 4,405,528  9/1983  Everly ............................ 260/465 F
4,483,800  11/1984  Everly et al. ................... 260/465 F

*Primary Examiner*—Dolph H. Torrence
*Attorney, Agent, or Firm*—Donald L. Johnson; John F. Sieberth; Patricia J. Hogan

[57] ABSTRACT

Novel 4-(α,α-dihydrocarbyl-α-cyano-methyl)-2,6-mono or dihydrocarbyl substituted phenols are prepared by reacting a 2,6-mono or dihydrocarbyl substituted phenol with a ketone and an alkali metal cyanide or an alkaline earth metal cyanide in an inert reaction solvent.

10 Claims, No Drawings

PREPARATION OF 4-(α,α-DIHYDROCARBYL-α-CYANO-METHYL)-PHENOLS

This application is a division of application Ser. No. 552,283, filed Nov. 16, 1983, abandoned.

TECHNICAL FIELD

The present invention relates to novel 4-(α,α-dihydrocarbyl-α-cyano-methyl)-2,6-mono or dihydrocarbyl substituted phenols and to a novel process for their preparation. The 4-(α,α-dihydrocarbyl-α-cyano-methyl)phenols of the present invention are deemed to have utility as antioxidants for oxidizable organic materials when such materials are exposed to oxidative, degradative conditions.

BACKGROUND

Methods are known for preparing 4-(α-alkyl-α-cyanomethyl)-2,6-disubstituted phenols. For example, the preparation of 4-(α-alkyl-α-cyano-methyl)-2,6-disubstituted phenol by reacting α-alkyl-4-hydroxy-3,5-di-tertiary-butylbenzyl halides with sodium cyanide is reported by A. A. Volod'kin et al., *Iz. Akad. Nauk. SSSR, Ser. Khim*, 1966, 1031. Also, the preparation of 4-(α-alkyl-α-cyano-methyl)-2,6-disubstituted phenol by the electrochemical reduction of the corresponding 2,6-disubstituted methylene-quinones is reported by L. I. Kudinova, et al., *Iz. Akad. Nauk. SSSR, Ser. Khim.*, 1978, 1313. U.S. Pat. No. 4,405,528 discloses a novel process for the synthesis of 4-(α-alkyl-α-cyanomethyl)-2,6-disubstituted phenols by reacting a 2,6-disubstituted phenol with a Friedel-Crafts addition agent in the presence of a Friedel-Crafts catalyst such as aluminum chloride to form the corresponding 4-(α-alkyl-α-oxomethyl)-2,6-disubstituted phenol, reducing the 4-(α-alkyl-α-oxomethyl)-2,6-disubstituted phenol to form the corresponding 4-(α-alkyl-α-hydroxy-methyl)-2,6-disubstituted phenol and thereafter reacting the 4-(α-alkyl-α-hydroxymethyl)-2,6-disubstituted phenol with an alkali metal or an alkaline earth metal cyanide to form the desired 4-(α-alkyl-α-cyano-methyl)-2,6-disubstituted phenol.

U.S. Pat. No. 4,483,800 discloses a method of preparing 4-(α-hydrocarbyl-α-cyano-methyl)-2,6-disubstituted phenols by reacting a 2,6-disubstituted phenol with an aldehyde and an alkali metal cyanide or an alkaline earth metal cyanide.

The synthesis of o- and p-hydroxy substituted phenylacetonitriles also is known and is reported in the literature. See for example, *Journal of Organic Chemistry*, Vol. 41, No. 14, 2502 (1976).

It has now been discovered that novel 4-(α,α-dihydrocarbyl-α-cyano-methyl)phenols can be prepared in a simple and straightforward manner. In this process, 4-(α,α-dihydrocarbyl-α-cyano-methyl)phenols are produced in a novel synthesis reaction and are deemed useful as antioxidants.

THE INVENTION

This invention thus involves in one embodiment the discovery that 4-(α,α-dihydrocarbyl-α-cyano-methyl)-phenols can be readily prepared by reacting a 2,6-mono or dihydrocarbyl substituted phenol with a ketone and an alkali metal cyanide or an alkaline earth metal cyanide in an inert reaction solvent to form the corresponding 4-(α,α-dihydrocarbyl-α-cyano-methyl)phenol.

The invention also involves in another embodiment that the 4-(α,α-dihydrocarbyl-α-cyano-methyl)phenols produced by the process of this invention are novel compounds.

The phenols which may be used as starting materials in the process of the invention are phenols having the general formula:

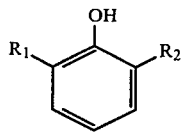

wherein $R_1$ and $R_2$ are the same or different and are hydrogen or hydrocarbyl radicals selected from the group consisting of alkyl, aralkyl and cyclic alkyl radicals with the provision that at least one of $R_1$ or $R_2$ must be other than hydrogen. These phenols are reacted in a liquid phase with a ketone and an alkali metal cyanide or an alkaline earth metal cyanide.

Typical examples of alkyl, aralkyl and cyclic alkyl radicals which $R_1$ and $R_2$ may be include any of the above radicals having any number of carbon atoms as long as these substituents do not interfere with the formation of the desired 4-(α,α-dihydrocarbyl-α-cyano-methyl)phenols or their antioxidant properties. These may include, for example, from 1 to 40 or more carbon atoms and the alkyl radicals may include primary, secondary or tertiary alkyl groups and cycloalkyl groups. Since the most readily available of the substituted phenols are those phenols having substituents of from 1 to about 8 carbon atoms, they are preferred, but the invention is not limited thereto. Examples of typical substituents include methyl, ethyl, propyl, isopropyl, the isomeric butyl radicals (i.e., n-butyl, isobutyl, cyclobutyl, t-butyl, etc.), the isomeric amyl radicals, the isomeric hexyl radicals, the isomeric decyl radicals, the isomeric hexadecyl radicals, the isomeric eicosyl radicals, the isomeric tricosyl radicals, the isomeric triacontyl radicals, etc. The alkyl radicals may be substituted with aryl, preferably monocyclic aryl radicals, or cycloalkyl radicals, for example, benzyl, phenylethyl, cyclohexylethyl, naphthylethyl, etc. Examples of aryl radicals are phenyl, tolyl, xylyl, biphenyl, naphthyl, methylnaphthyl, ethylphenyl, cyclohexylphenyl, etc. Because the phenols in which the R substituents are methyl, ethyl, propyl, butyl, sec-butyl, isopropyl, t-butyl, amyl, sec-amyl, t-amyl, hexyl, heptyl, octyl, etc., or phenyl are either readily available commercially or easily made and are ideally suited for the process, the most preferred substituents are where $R_1$ or $R_2$ is a lower alkyl group (i.e., from 1 to about 8 carbon atoms) or phenyl.

Examples of phenols having the R substituent groups noted above which are preferred starting materials include 2,6-di-methylphenol, 2,6-di-sec-butylphenol, 2,6-diisopropylphenol, 2,6-di-sec-octyl-phenol, 2,6-di-(α-methylbenzyl)phenol, 2-amyl-6-methyl-phenol, 2,6-dibenzylphenol, 2-methyl-6-benzylphenol, and the like. A particularly preferred phenol reactant for use in the practice of the process is 2,6-di-tert-butylphenol.

Substituent R groups other than those previously listed such as aryl, chlorine, bromine, fluorine, nitro groups and the like may be present at the 2- and 6-positions in the aromatic phenol compound providing they do not adversely affect the formation of the 4-(α,α- dihydrocarbyl-α-cyano-methyl)phenols of the present invention or their properties as antioxidants.

The ketone reactants used in the present process are ketones having the formula:

wherein $R_3$ and $R_4$ are the same or different and are hydrocarbyl radicals or substituted hydrocarbyl radicals having any number of carbon atoms as long as the substituents do not interfere with the formation of the desired phenols of the present invention or their antioxidant properties. Preferred hydrocarbyl radicals are those which contain up to about 30 carbon atoms. The most preferred hydrocarbyl radicals are those that contain up to about 20 carbon atoms. For purposes of this invention, a hydrocarbyl radical can be defined as an organic group solely composed of hydrogen and carbon atoms. Some non-limiting representative examples of hydrocarbyl radicals are alkyl, cycloalkyl, alkenyl, aralkyl, alkaryl, and aryl.

Examples of suitable alkyl groups are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl, dodecyl, and the like.

Some examples of cycloalkyl groups are cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropylethyl, α-cyclobutylpropyl, β-cyclobutylpropyl, and similar alkyl derivatives of the higher cycloalkyls.

Some examples of alkenyl groups are ethenyl, 1-propenyl, 2-propenyl, isopropenyl, 1-butenyl, 2-butenyl, 3-butenyl, and the corresponding branched-chain isomers thereof as for example, 1-isobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1-butenyl, 2,3-dimethyl-1-butenyl, 2,3-dimethyl-2-butenyl, 2,3-dimethyl-3-butenyl, 1-methyl-1-ethyl-2-propenyl, and the like.

Examples of alkaryl groups are tolyl, 2,3-xylyl, 2,4-xylyl, 2,5-xylyl, 2,6-xylyl, 3,4-xylyl, 3,5-xylyl; o, m, and p-cumenyl, mesityl, o, m, and p-ethylphenyl, 2-methyl-1-naphthyl, 3-methyl-naphthyl, 4-methyl-1-naphthyl, 5-methyl-2-naphthyl, 6-methyl-3-naphthyl, 7-methyl-1-naphthyl, 9-methyl-4-naphthyl, 1-ethyl-2-naphthyl, and its various positional isomers and the like.

Examples of aryl groups which may be present in the above general formula are phenyl, naphthyl, and the like.

Examples of aralkyl groups are benzyl, phenylethyl, 1-phenylpropyl, 2-phenylpropyl, 3-phenylpropyl, 1- and 2-isomers of phenylisopropyl, 1-, 2-, and 3-isomers of phenylbutyl, and the like.

The substituted hydrocarbyl radicals are hydrocarbyl radicals which contain substituents such as halogen, hydroxyl, carboxyl, amino, or amide radicals.

As mentioned above, the hydrocarbyl groups may be halogen substituted. Thus, chlorine, bromine, iodine, and fluorine may be substituted on the alkyl, cycloalkyl, alkenyl, alkaryl, aryl, and aralkyl groups which are present. Non-limiting examples of such substituted groups are chloromethyl, chloroethyl, bromoethyl, 2-fluoro-1,2-dibromoethyl, 1-iodopropyl, 2-fluoropropyl, 1-chlorobutyl, 2-bromobutyl, 2-iodo-2-methylpropyl, 1-chloropentyl, 3-fluoro-2-methylbutyl, 3-iodo-2-methylbutyl, 1-chloro-2,2-dimethylpropyl, 2-chloroheptyl, 3-fluorononyl, 1-chlorododecyl, and the like. Examples of halogenated cycloalkyl groups are chlorocyclopropyl, chlorocyclohexyl, 1,2-dichlorohexyl, bromocyclobutyl, iodocyclohexyl, and the like.

Examples of halogen-substituted alkenyl groups are bromoethenyl, chloroethenyl, iodoethenyl, 1-bromododecenyl, and the like.

Examples of halogenated alkaryl groups are chloro-p-tolyl, chloro-o-tolyl, chloro-m-tolyl, 2-bromo-2,3-xylyl, 4-bromo-2,3-xylyl, 5-bromo-2,4-xylyl, 2-bromo-4,5-xylyl, o-, m-, and p-tolyl, 3-bromomesityl, chloro(methyl)-1-naphthyl, iodo(ethyl)-1-naphthyl, all positional isomers of the above, and the like.

Examples of halogen substituted aryl groups are bromophenyl, 2-bromo-1-naphthyl, 3-bromo-1-naphthyl and all positional isomers thereof, 2,4-dibromophenyl, 2,3-dibromophenyl, 2,5-dibromophenyl, 2,3,4,5-tetrabromophenyl, 2,3,5,6-tetrabromophenyl, pentabromophenyl, all isomers of chlorophenyl, and all isomers of multichlorophenyl, 2-chloro-1-naphthyl and the remaining isomers thereof, 2,3-dichloro-1-naphthyl, 2,4-dichloro-1-naphthyl and the remaining positional isomers of dichloronaphthyl, 2,3,4,5-tetrachloro-1-naphthyl.

Amine groups may also be substituted on the hydrocarbyl groups. Some non-limiting illustrative examples of hydrocarbyl groups containing amine substituents are aminomethyl, 2-aminoethyl, 2,2-diaminoethyl, 2-aminoisopropyl, 5-aminopentyl, 1,2-aminododecyl, 1,2-diaminoethyl, 1,5-diaminopentyl, aminocyclobutyl, aminocyclohexyl, 3-amino-1-propen-1-yl, 5-amino-2-penten-1-yl, aminophenyl, (methylamino)phenyl, 2-amino-o-tolyl, 4-amino-m-tolyl, 3-amino-p-tolyl, and other positional isomers, various isomers of diaminophenyl, amino-2,5-xylyl, and various positional isomers thereof, 2-amino-1-naphthyl, 3-amino-1-naphthyl, 2-amino-3-methyl-1-naphthyl, 2,3-diamino-5-ethyl-1-naphthyl, and the like.

The hydrocarbyl groups may contain amide groups which may be illustrated by such non-limiting examples as: carbamoylmethyl, 2-carbamoylethyl, 4-carbamoylbutyl, 8-carbamoyl-2-ethyloctyl, 1,4-dicarbamoylbutyl, carbamoylcyclopentyl, carbamoylcyclohexyl, 2-carbamoyl-o-tolyl, 2-carbamoyl-m-tolyl, 3-carbamoyl-o-tolyl, (carbamoylmethyl)phenyl, (2-carbamoylethyl)-benzyl, o-, m-, and p-(carbamoylethyl)phenyl, and the like.

The alkali metal cyanide and alkaline earth metal cyanide reactants used in the present process may include sodium cyanide, potassium cyanide, lithium cyanide, magnesium cyanide and calcium cyanide. Ammonium cyanide also may be used in the practice of the process as well as hydrogen cyanide. Sodium cyanide is a preferred cyanide reactant.

The reaction is carried out in the liquid phase which is provided by using a solvent which is inert under the reaction conditions. That is, the rection is carried out in the presence of a solvent which does not enter into the reaction. Preferred solvents are aprotic solvents which include ethers such as diethyl ether, dibutyl ether, 1-ethoxyhexane, tetrahydrofuran, 1,4-dioxane, 1,3-dioxolane, diglyme, 1,2-diethoxyethane and tertiary amines such as pyridine, N-ethylpiperidine, triethylamine, tributylamine, N,N-diphenyl-N-methyl amine, N,N-dimethylaniline, etc. Especially preferred solvents are dipolar aprotic solvents such as dimethyl sulfoxide, N,N-dimethylformamide, N,N-dimethylacetamide, dimethyl sufone, tetramethylene sulfone, N-methlpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. Additionally, lower alkanols having up to about 6 carbon atoms also may be used. These include methanol, ethanol, n-propanol, isopropyl alcohol, n-butanol, sec-butyl alcohol, tert-butyl alcohol, n-pentanol, isopentyl alcohol, n-hexanol and isohexyl alcohol. In addition, a small amount of water may be added to the reaction mixture to facilitate the solubilization of the cyanide-containing reactant in the mixture.

The reaction is readily conducted by placing the substituted phenolic reactant and the other reaction mixture components in a reaction vessel having agitation means. The process is preferably conducted in a substantially anhydrous reaction system, and accordingly, the components of the reaction system should be brought together and maintained under a substantially dry, inert atmosphere. Thus, while it is possible to conduct this process in the presence of air or moisture, as when water is added to the reaction mixture, it is desirable to maintain the reaction system under an atmosphere of dry nitrogen or the like.

The mode of addition is not particularly critical. Accordingly, it is convenient to add the phenol reactant to a mixture of the other materials, add the ketone reactant to a mixture of the other materials, add the cyanide reactant to a mixture of the other materials, introduce all ingredients simultaneously into the reaction zone, or the like.

Although the reaction will proceed at a very slow rate at ambient temperature, it is convenient to conduct the reaction at an elevated temperature of at least about 50° C. up to just short of the decomposition temperature of any of the reactants or the products. Ambient atmospheric pressure can be used or pressures lower or higher than ambient pressure can be used. However, there is no advantage of using less than ambient pressure. Higher than ambient pressure conditions are usually used if temperatures higher than the boiling point at atmospheric conditions of the reaction mixture are being used. However, by proper choice of the solvent to form the liquid phase desired, temperatures can be reached within the range of about 50° C. up to the reflux temperature of the reaction mixture at ambient atmospheric conditions which give a suitable reaction rate.

Recovery of the product is achieved by conventional means such as evaporation and water wash or extraction with a suitable organic solvent.

For best results, it is desirable to employ an excess of both the ketone and cyanide reactants relative to the phenol reactant. Normally, the reaction system will contain at least one molar equivalent of ketone and one molar equivalent of cyanide per mole of phenol reactant and preferably the molar ratio of the ketone and the cyanide reactants to the phenol is 2 or more.

The 4-($\alpha,\alpha$-dihydrocarbyl-$\alpha$-cyano-methyl)phenols prepared by the process of the present invention are deemed to have antioxidant properties capable of stabilizing polymers normally subject to oxidative degradation when incorporated into the polymers using conventional techniques such as by addition to polymer lattices; or by addition to solid polymers on a mill or Banbury. Further, the novel compounds of this invention are deemed to be effective antioxidants in both leaded and unleaded gasolines made from a wide variety of base stocks and for engine and industrial oils which are derived from crude petroleum or produced synthetically.

Since the 4-($\alpha,\alpha$-dihydrocarbyl-$\alpha$-cyano-methyl)-phenols of the present process are believed to be novel compounds, in a still further embodiment of the present invention, there is provided, as new compositions of matter, compounds of the general formula:

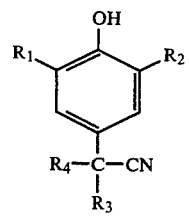

wherein $R_1$ and $R_2$ are the same or different and are hydrogen or hydrocarbyl radicals selected from the group consisting of alkyl, aralkyl and cyclic alkyl radicals with the provision that at least one of $R_1$ or $R_2$ must be other than hydrogen and $R_3$ and $R_4$ are the same or different and are hydrocarbyl radicals or substituted hydrocarbyl radicals, preferably having up to about 30 carbon atoms and selected from alkyl, cycloalkyl, alkenyl, aralkyl, alkaryl and aryl radicals.

The practice of this invention will be still further apparent by the following illustrative examples.

EXAMPLE 1

Preparation of 4-$\alpha,\alpha$-Dimethyl-$\alpha$-Cyano-Methyl)-2,6-Di-Tertiary-Butyl Phenol 2,6-di-t-butyl phenol (2.06 g; 10 mmoles), acetone (1.39 g; 24 mmoles), sodium cyanide (1.47 g; 30 mmoles) and dimethylformamide (3 mLs) were charged to an autoclave and heated to 140° C. (oil bath temperature) and held at that temperature for 9 hours. The resultant reaction mixture was allowed to cool to ambient temperature and an aliquot of the product was analyzed by VPC and HPLC. Analysis indicated that approximately 11% of 4-($\alpha,\alpha$-dimethyl-$\alpha$-cyano-methyl)2,6-di-t-butyl phenol was present in the product.

EXAMPLE 2

Preparation of 4-($\alpha,\alpha$-Dimethyl-$\alpha$-Cyano-Methyl)-2,6-Di-Tertiary-Butyl Phenol 2,6-di-t-butyl phenol (1.03 g; 5 mmoles), acetone (1.39 g; 24 mmoles), sodium cyanide (1.47 g; 30 mmoles) and dimethylformamide (3 mLs) were charged to an autoclave and heated to 140° C. (oil bath temperature) for approximately 64 hours. The resultant reaction mixture was allowed to cool to ambient temperature and an aliquot of the product was analyzed by HPLC. Analysis indicated that approximately 66% of 4-($\alpha,\alpha$-dimethyl-$\alpha$-cyano-methyl)2,6-di-t-butyl phenol was present in the product.

Having disclosed the process of the present invention, one skilled in the art can readily envision various modifications and changes which are nevertheless within the scope of the invention. Therefore, it is desired that the process of this invention be limited only by the lawful scope of the appended claims.

I claim:

1. A process for the preparation of 4-α,α-dihydrocarbyl-α-cyano-methyl)-2,6-mono or dihydrocarbyl substituted phenols which comprises reacting the corresponding 2,6-mono or dihydrocarbyl substituted phenol with a ketone and an alkali metal cyanide or an alkaline earth metal cyanide in an inert reaction solvent and thereafter recovering said 4-(α,α-dihydrocarbyl-α-cyano-methyl)phenol.

2. A process for the preparation of 4-α,α-dihydrocarbyl-α-cyano-methyl)phenols having the formula:

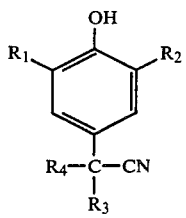

wherein $R_1$ and $R_2$ are the same or different and are hydrogen or hydrocarbyl radicals selected from the group consisting of alkyl, aralkyl and cyclic alkyl radicals with the provision that at least one of $R_1$ or $R_2$ must be other than hydrogen and $R_3$ and $R_4$ are the same or different and are hydrocarbyl radicals or substituted hydrocarbyl radicals which comprises reacting a 2,6-mono or dihydrocarbyl substituted phenol having the formula:

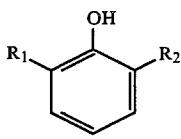

wherein $R_1$ and $R_2$ are as defined above with a ketone having the formula:

$$R_3COR_4$$

wherein $R_3$ and $R_4$ are as defined above and an alkali metal cyanide or an alkaline earth metal cyanide in an inert solvent.

3. The process of claim 2 wherein $R_1$ and $R_2$ are the same or different and are hydrogen or hydrocarbyl radicals selected from the group consisting of alkyl, aralkyl or cyclic alkyl containing from 1 to about 40 carbon atoms with the provision that at least one of $R_1$ or $R_2$ must be other than hydrogen and $R_3$ and $R_4$ are the same or different and are hydrocarbyl or substituted hydrocarbyl radicals having up to about 30 carbon atoms.

4. The process of claim 2 wherein $R_1$ and $R_2$ are the same or different and are hydrogen or a hydrocarbyl radicals selected from methyl, ethyl, n-propyl, isopropyl and t-butyl with the provision that at least one of $R_1$ or $R_2$ must be other than hydrogen and $R_3$ and $R_4$ are the same or different and are hydrocarbyl radicals selected from methyl, ethyl, n-propyl, and isopropyl.

5. The process of claim 1 wherein the alkali metal cyanide is sodium cyanide.

6. The process of claim 1 wherein the solvent is a dipolar aprotic solvent.

7. The process of claim 6 wherein the solvent is selected from the group consisting of dimethyl sulfoxide, N,N-dimethylformamide, N,N-dimethylacetamide, dimethyl sulfone, tetramethylene sulfone, N-methylpyrrolidinone and acetonitrile.

8. The process of claim 6 wherein the solvent is selected from the group consisting of a lower alkanol having from 1 to about 6 carbon atoms.

9. The process of claim 1 wherein the reaction is carried out at an elevated temperature.

10. The process of claim 9 wherein the process is carried out at a temperature of at least 50° C.

* * * * *